United States Patent
Yoon et al.

(10) Patent No.: US 11,833,351 B2
(45) Date of Patent: Dec. 5, 2023

(54) APPARATUS AND METHOD FOR ALTERNATING ELECTRIC FIELDS THERAPY USING AN OPTIMIZATION ALGORITHM

(71) Applicant: FIELDCURE CO., LTD., Seoul (KR)

(72) Inventors: Myong Geun Yoon, Gyeonggi-do (KR); Ji Won Sung, Gyeonggi-do (KR); Jae Hyeon Seo, Seoul (KR)

(73) Assignee: FIELDCURE CO., LTD., Seoul (KR)

( * ) Notice: Subject to any disclaimer, the term of this patent is extended or adjusted under 35 U.S.C. 154(b) by 121 days.

(21) Appl. No.: 17/257,252

(22) PCT Filed: Feb. 20, 2019

(86) PCT No.: PCT/KR2019/002009
§ 371 (c)(1),
(2) Date: Dec. 30, 2020

(87) PCT Pub. No.: WO2020/009306
PCT Pub. Date: Jan. 9, 2020

(65) Prior Publication Data
US 2021/0228896 A1     Jul. 29, 2021

(30) Foreign Application Priority Data

Jul. 3, 2018  (KR) .................. 10-2018-0077093
Aug. 21, 2018 (KR) .................. 10-2018-0097291

(51) Int. Cl.
*A61N 1/36*     (2006.01)
*A61N 1/40*     (2006.01)
*G06F 18/24*    (2023.01)

(52) U.S. Cl.
CPC ........... *A61N 1/36002* (2017.08); *A61N 1/40* (2013.01); *G06F 18/24* (2023.01)

(58) Field of Classification Search
CPC .................................. A61N 1/36002
See application file for complete search history.

(56) References Cited

U.S. PATENT DOCUMENTS 7,146,210 B2    12/2006  Palti
2001/0044643 A1* 11/2001  Litovitz ............. A61N 1/40
                                                607/100

(Continued)

FOREIGN PATENT DOCUMENTS

KR       10-1688520        12/2016
KR    10-2018-0072811       6/2018

(Continued)

OTHER PUBLICATIONS

International Search Report dated Jun. 3, 2019 for PCT/KR2019/002009.
European Search Report dated Feb. 28, 2022 for EP 19831280.

*Primary Examiner* — Michael W Kahelin

(57) ABSTRACT

The present disclosure describes an apparatus and method for alternating electric fields therapy using an optimization algorithm, and an apparatus for alternating electric fields therapy for treating tumors in a patient by applying electric fields to the tumors and normal tissues using one or more pairs of electrode pads containing most of the electrodes and including an image classifier to classify at least one organ in the patient's image for each organ, and an electric field optimizer to set the number and position of the applied electrodes based on the classified tumors and normal tissues, arrange the electrodes on electrode pads of preset size, and determine different magnitudes of voltage for the set of electrodes.

7 Claims, 3 Drawing Sheets

(56) References Cited

U.S. PATENT DOCUMENTS

| | | |
|---|---|---|
| 2004/0176804 A1* | 9/2004 | Palti ................. A61N 1/326 607/2 |
| 2004/0177804 A1 | 9/2004 | Palti |
| 2005/0041843 A1* | 2/2005 | Sawyer ............ A61N 5/1049 382/128 |
| 2008/0013687 A1* | 1/2008 | Maurer, Jr. ........... G21K 1/046 600/1 |
| 2010/0179621 A1 | 7/2010 | Palti |
| 2010/0250209 A1* | 9/2010 | Pearson ........... A61B 18/1206 703/2 |
| 2017/0161454 A1 | 6/2017 | Grill et al. |
| 2018/0160933 A1 | 6/2018 | Urman et al. |

FOREIGN PATENT DOCUMENTS

| | | |
|---|---|---|
| WO | WO 2015-111091 | 7/2015 |
| WO | WO 2017-072706 | 5/2017 |
| WO | WO 2018-106843 | 6/2018 |

\* cited by examiner

APPARATUS AND METHOD FOR ALTERNATING ELECTRIC FIELDS THERAPY USING AN OPTIMIZATION ALGORITHM

This application claims the priority of Korean Patent Application No. 10-2018-0077093, filed on Jul. 3, 2018, and 10-2018-0097291, filed on Aug. 21, 2018 in the KIPO (Korean Intellectual Property Office), the disclosure of which is incorporated herein entirely by reference. Further, this application is the National Stage application of International Application No. PCT/KR2019/002009, filed Feb. 20, 2019, which designates the United States and was published in Korean. Each of these applications is hereby incorporated by reference in their entirety into the present application.

TECHNICAL FIELD

The present disclosure describes an apparatus and method for alternating electric fields therapy using an optimization algorithm. In particular, this algorithm is designed to optimize the magnitude of electric fields, such that the prescribed or higher electric field intensity is applied to tumors in a patient's body while minimizing the electric field intensity transmitted to normal tissues.

BACKGROUND ART

Electromagnetic waves are used to treat tumors, with the effects depending on the frequency of the waves. X-rays, which have a frequency of about $10^{10}$ MHz, treat cancers by breaking the DNA double helix of cancer cells, causing cell death. By contrast, application of electromagnetic waves with frequencies in the range of about 10 MHz to tumors in the human body produces heat inside the tumors.

Tumor therapy using electromagnetic waves in the range of 100 to 300 kHz is known as Tumor Treating Fields (TTFields). This technology treats tumors by delaying cell division to induce cell death. Although introduced less than 10 years ago, TTFields is currently used to treat patients in about 1000 treatment centers worldwide.

Although TTFields greatly affects cells that are dividing, it has little effect on normal cells that divide more slowly than tumor cells or on cells that virtually do not divide. Only a few studies to date have described the effects of TTFields on normal cells or the effects of electric fields on each major organ in the human body. Additionally, because this technology has been used for only 10 years, the potential risks of long-term side effects remain unclear.

Current treatment involves placing the electrodes at positions to apply maximal electric fields to tumors, while, at the same time, applying minimal electric fields to normal tissues. However, the same voltage is applied to all electrodes, which may result in the unnecessary application of electric fields to normal tissues.

Accordingly, the present disclosure describes an apparatus and method for applying alternating electric fields therapy to treat tumors. In this method, not only the position of the electrodes but the voltage applied to each is adjusted through an optimization algorithm to further reduce electric fields unnecessarily transmitted to normal tissues.

DISCLOSURE OF THE INVENTION

Technical Problem

The present disclosure describes an apparatus and method for alternating electric fields therapy using an algorithm that optimizes the magnitude of the electric fields applied to tumors while minimizing the electric field intensity applied to normal tissues.

The objective of the present disclosure is not limited to the above-mentioned objective, and other objectives not mentioned herein will be clearly understood by those skilled in the art from the following description.

Technical Solution

To achieve the above-described objective, an apparatus for alternating electric fields therapy to treat tumors in a patient is required. This apparatus applies electric fields to tumors and normal tissues using one or more pairs of electrode pads, with most of these electrodes being arranged according to an embodiment of the present disclosure. This includes an image classifier to classify at least one organ in patient imaging of each organ, as well as an electric field optimizer to set the number and position of the applied electrodes, based on the classification of tissues as tumors or normal tissues. These electrodes are arranged on electrode pads of preset sizes, and the magnitudes of voltage for the set electrodes determined.

The electric field optimizer can set the magnitude of the voltage applied to most electrodes based on least one of the tumor types to be treated, the position of these tumors, and the boundary conditions with normal tissues.

This electric field optimizer can calculate the magnitude of the voltage to be applied to the tumors, with this voltage being at least the prescribed electric field intensity, while applying a minimal electric field intensity to normal organs.

This electric field optimizer can set the electric field limit value according to the importance of the organs, thereby allowing the electrodes to transmit the preset or lower electric field limit value.

This electric field optimizer can have an object function, which is set using the intensity of at least one of the electric fields transmitted to tumors or normal organs, with a weighting for each normal organ or an electric field limit value.

One pair of electrode pads can form a ground.

This method for alternating electric fields therapy to treat tumors in patients by applying electric fields to the tumors and normal tissues involves one or more pairs of electrode pads, with most electrodes being arranged according to an embodiment of the present disclosure. This method includes patient imaging and classifying the image for each organ, creating at least one treatment plan by arranging the number and position of electrodes on the electrode pads of a preset size based on the tumors in the patient and the boundary conditions between the tumors and normal tissues. The magnitude of the voltage applied to most of the electrodes is set using an electric field optimizer. Each formulated treatment plan is subsequently analyzed and evaluated and the tumor treated by applying the set voltage to most of the electrodes under the conditions determined to be optimal in the analyzed treatment plan.

The magnitude of voltage applied to the electrodes can be calculated using an electric field optimizer to apply prescribed or higher electric fields to the tumors and minimal electric fields to normal tissues.

The voltage applied to the electrodes can be between 0 V and 150 V and the frequency between 100 kHz and 300 kHz.

The magnitude of the voltage to be applied to the electrodes can be determined based on the magnitude of the electric fields prescribed for the tumors, the weighting assigned to each organ and/or the preset electric field limit.

Advantageous Effects

The apparatus and method for alternating electric fields therapy using an optimization algorithm, as described in the present disclosure, apply different electric fields to tumors and normal tissues. The voltage applied to each electrode using the optimization algorithm was designed to reduce the magnitude of electric fields transmitted to the normal tissues, so that it was less than the magnitude applied to the tumors, thereby reducing the risk of side effects of treatment and increasing the probability of treatment success.

The effects of the present disclosure are not limited to the above-mentioned effects, and other effects not mentioned herein will be clearly understood by those skilled in the art from the following description.

BEST MODE FOR CARRYING OUT THE INVENTION

Hereinafter, exemplary embodiments of the present disclosure will be described in detail with reference to the accompanying drawings. Identical symbols represent identical elements in the accompanying drawings. Detailed descriptions of known functions and elements that make the subject matter of the present disclosure ambiguous are omitted. Similarly, some elements are exaggerated, omitted or shown schematically in the accompanying drawings.

Unless the context clearly indicates otherwise, "comprises" specifies the presence of stated elements but does not preclude the presence or addition of one or more other elements. In addition, throughout the specification, when an element is referred to as being "on" another element, it indicates that the element is disposed on or below the other element, but it does not necessarily indicate the gravitational direction.

Figure 1:
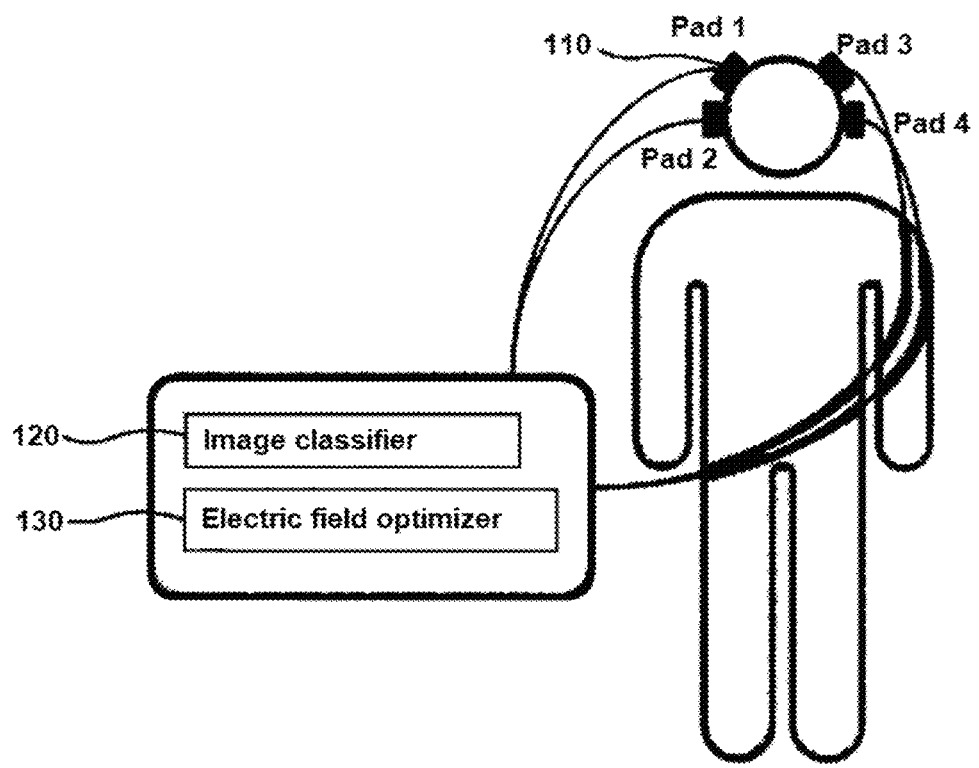
FIG. 1 shows a conceptual diagram of an apparatus for alternating electric fields therapy using an optimization algorithm, as embodied in the present disclosure.
Figure 2:
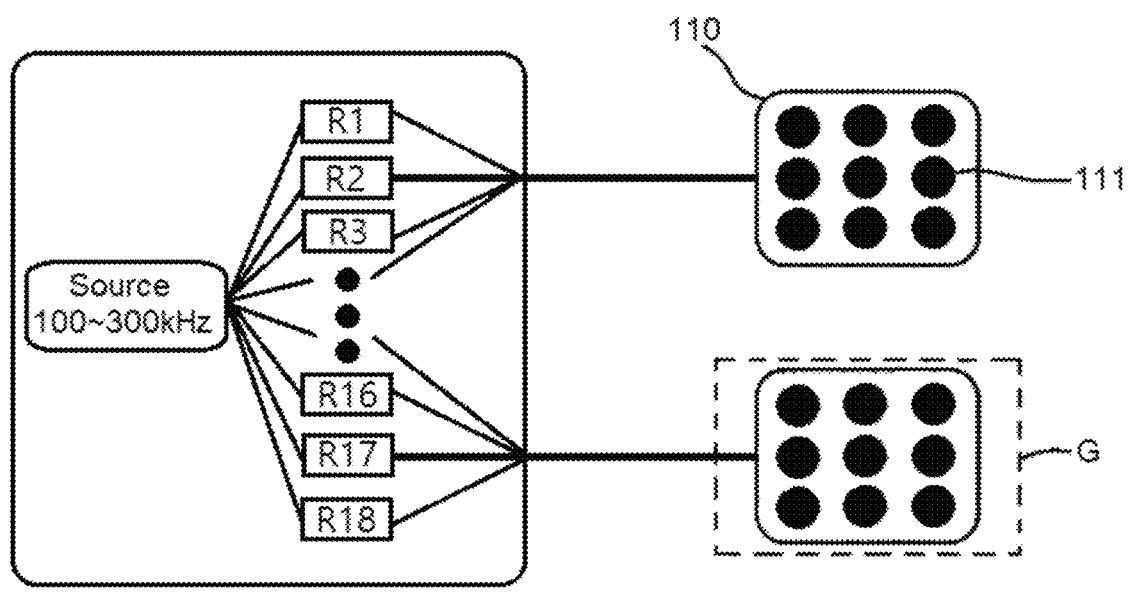
FIG. 2 shows a conceptual diagram showing the arrangement of electrodes of an apparatus for alternating electric fields, as embodied in the present disclosure.

FIG. 1 shows a conceptual diagram of an apparatus for alternating electric fields therapy using an optimization algorithm, as embodied in the present disclosure, and FIG. 2 shows a conceptual diagram showing the arrangement of electrodes of an apparatus for alternating electric fields as describe in the present disclosure.

With reference to FIGS. 1 and 2, the apparatus for alternating electric fields using an optimization algorithm, as embodied in the present disclosure, is configured to treat tumors in a patient by applying voltage to form separate electric fields in tumors and normal tissues. This apparatus includes a pair of electrode pads 110, an image classifier 120 and an electric field optimizer 130.

The pair of electrode pads 110 includes most of the electrodes 111, which are variously arranged according to the shape of the electrode pads 110. Although FIG. 2 shows the electrodes 111 arranged in a 3×3 matrix, as illustrated, the numbers of electrodes 111 and the interval between them may be modified through the electric field optimizer 130, as described below. The shape and arrangement are not limited to those shown in FIG. 2. Although two pairs of electrode pads 110 are shown, the number of electrode pads 110 may increase or decrease depending on the patient's treatment conditions.

The magnitudes of the electric fields transmitted to the tumors and normal tissues can be altered by arranging the configuration of the electrodes 111 to adjust the applied frequency and voltage, thereby providing effective treatment based on the boundary conditions between a patient's tumors and normal tissues. For example, the pair of electrode pads 110 may form the ground G on one of the pair.

The image classifier 120 serves to classify at least one organ in a patient's image. This image may be a magnetic resonance (MR) or computed tomography (CT) image. Each MR or CT image includes the tumors together with a variety of organs. In this instance, the image classifier 120 classifies most of the images for each organ, and determines the distance between normal tissues and tumors along with their positional relationships. The image classifier 120 may use the data to adjust the size of the pair of electrode pads 110 or the arrangement of the electrodes by automatically classifying them according to the organ or by setting the boundaries for each organ according to the user definition. The image classifier 120 can reconstruct each image into a 3-dimensional image of each organ and clearly determine their positional relationships.

The electric field optimizer 130 sets the number and position of applied electrodes based on the classified tumors and normal tissues, arranges the electrodes on electrode pads 110 of preset size, and determines the magnitudes of voltage for the set electrodes. That is, the electric field optimizer 130 sets the magnitude of voltage applied to the electrodes by considering the classified tumors and normal tissues and the conditions of the tumors.

The electric field optimizer 130 can set the magnitude of voltage applied to the electrodes by considering at least one of the types of tumors to be treated, the position of the tumors, and the boundary conditions between the tumors and normal tissues. In this instance, the electric field optimizer 130 can set the electrode weighting as a variable, divide most of the electrodes into those applying voltage and a ground electrode, and set the frequency of most of the electrodes depending on the type of tumors. For example, the weighting and voltage of each electrode can be calculated by setting the frequency to 200 kHz for glioblastomas and 150 kHz for lung cancers.

Thus, when transmitting the adjusted electric fields into the body, different electric fields are applied to tumors and normal tissues, thereby reducing the magnitude of electric fields transmitted to normal tissues so that they are lower than the magnitude transmitted to tumors, reducing the risk of side effects of treatment and increasing the probability of treatment success.

The electric field optimizer 130 can have an object function that is set based on the intensity of at least one of the electric fields transmitted to the tumors or the normal organs, the weighting assigned to each normal organ or the electric field limit. Additionally, the electric field optimizer 130 can set the electric field limit according to the importance of organs, allowing the electrodes to transmit the preset or lower electric field. Here, the electric field limit refers to the range of electric fields set to prevent the preset or higher electric field intensity from being transmitted to normal organs.

When electric fields intensities equal to or higher than those prescribed are applied to the tumors, the object function can adjust the electric field intensity to apply minimal electric fields to the major organs of normal tissues. Here, the prescribed electric field is the magnitude of electric fields for transmitting a predetermined or higher electric field intensity to the total volume of the tumors, and the electric field limit is the magnitude of electric fields for transmitting the predetermined or lower electric field intensity to the total volume of the normal organs.

For example, in alternating electric fields therapy, a treatment plan can be created through optimization to apply a prescribed electric field intensity of 1.5 V/cm to tumors and transmit an electric field intensity limit of ≤0.5 V/cm to the total volume of major organs. In this instance, the average electric field intensity is the average transmitted to one organ, with the same electric field not transmitted to all parts of that organ. Because the transmitted electric field intensity is different for each microvolume, the average electric field intensity is determined for individual organs.

After setting an electric field at position $E_i$, spaced a predetermined distance from the tumor, as in Equation 1, the electric field intensity can be calculated from the conditions shown in Equations 2 to 4.

$$E_i = \sum_{i=1}^{n} w_j e_{ij} \quad \text{[Equation 1]}$$

Here, $E_i$ is the electric field intensity value at the $i^{th}$ position, $w_j$ is the weighting of the $j^{th}$ electrode, and $e_{ij}$ is the electric field intensity transmitted to the $i^{th}$ position by the $j^{th}$ electrode.

Equation 2 calculates electric fields based on the prescribed electric field intensity.

$$f = \sum_{i=1}^{N}(E_i - E_0)^2 \quad \text{[Equation 2]}$$

Here, $E_0$ is the prescribed electric field intensity.

Equation 3 calculates electric fields based on the object function f, considering that the weighting was dependent on the importance of organs and the electric field intensity limit of normal organs. The electric field intensity limit is a constant that differs depending on the importance of organs.

$$f = W_1 \sum_{j=1}^{a} H(E_j - E_0^{organ1})(E_j - E_0^{organ1})^2 +$$
$$W_2 \sum_{k=1}^{b} H(E_k - E_0^{organ2})(E_k - E_0^{organ2})^2 +$$
$$\ldots + W_N \sum_{u=1}^{g} H(E_u - E_0^{organN})(E_u - E_0^{organN})^2 \quad \text{[Equation 3]}$$

-continued

Here, if $E_j > E_0^{organN}$, $H(E_j - E_0^{organN}) = 1$ if $E_j \leq E_0^{organN}$, $H(E_j - E_0^{organN}) = 0$ Here, $W_N$ is the weighting for each organ and $E_o^{organN}$ is the electric field intensity limit for the $N^{th}$ normal organ.

Equation 4 calculates electric fields by considering the weighting for each organ and the average electric field intensity of the $N^{th}$ normal organ.

$$f = W_1 E_{ave}^{organ1} + W_2 E_{ave}^{organ2} + \ldots + W_N E_{ave}^{organN} \quad \text{[Equation 4]}$$

Here, $W_N$ is the weighting for each organ and $E_{ave}^{organN}$ is the average electric field intensity of the $N^{th}$ normal organ.

As such, the object function for calculating the electric fields acting on normal organs is not limited to the above Equation and differs depending on the type and position of tumors.

The present disclosure sets the electric field based on a voltage of 0 V to 150 V applied to the electrodes and a frequency of 100 kHz to 300 kHz, as well as on the position of the tumors and the importance of each organ. This electric field intensity is converted to the voltage applied to the electrodes.

The voltage range of 0 V to 150 V may be similar to the range used for conventional treatment apparatuses, but the present disclosure sets the arrangement and position of the electrodes by considering the position of the tumors and normal organs and their relationship, and applies different magnitudes of therapeutic and general electric fields to most of the electrodes, preventing damage to normal tissues.

Figure 3:
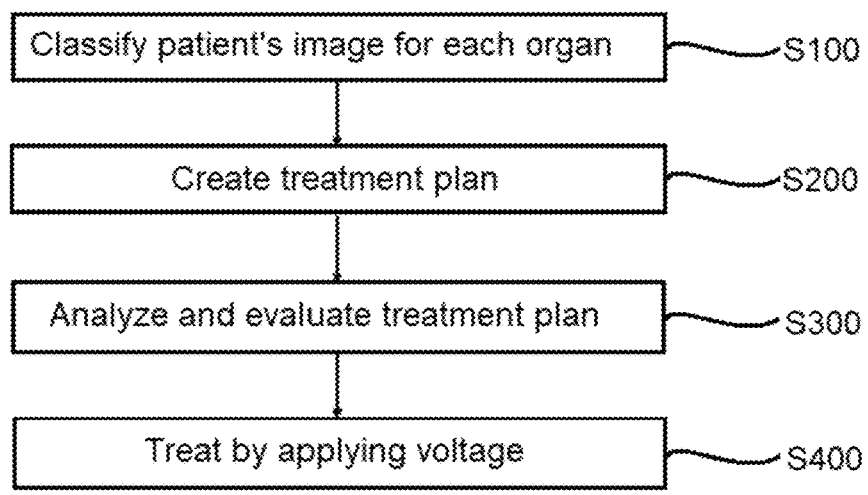
FIG. 3 shows a flowchart of a method for alternating electric fields therapy using an optimization algorithm, as embodied in the present disclosure.

FIG. 3 shows a flowchart of a method for alternating electric fields therapy using an optimization algorithm according to an embodiment of the present disclosure. This method treats tumors in a patient by transmitting electric fields to the tumors and normal tissues using one or more pairs of electrode pads that include most of the electrodes.

First, an image is retrieved based on imaging of the patient, and the retrieved image is classified for each organ (S100). Organs may be classified more effectively according to their importance by setting the resolution range for each organ individually.

Subsequently, at least one treatment plan is created by arranging the number and position of electrodes on the electrode pads of a preset size, based on the patient's tumors and the boundary conditions between the tumors and normal tissues, and by setting the magnitude of voltage applied to most electrodes through the electric field optimizer (S200). In this example, three or more treatment plans can be created, with these plans adapted for different sizes and numbers of electrodes.

Although the electrodes can be arranged in a matrix (FIG. 2), they can also be arranged in other configurations; for example, asymmetrically or at different intervals. In this example, the pair of electrodes facing each other may be placed at the same position. Additionally, the applied voltage and frequency may differ between tumors and normal tissues, with voltages ranging from 0 V to 150 V and frequencies from 100 kHz to 300 kHz.

The created treatment plans are analyzed and evaluated (S300). The conditions for optimal results may be determined by individually analyzing and evaluating each of the treatment plans.

Finally, the patient is treated by applying the set voltage to most of the electrodes under the optimal conditions determined by the analyzed treatment plans (S400).

Figure 4:
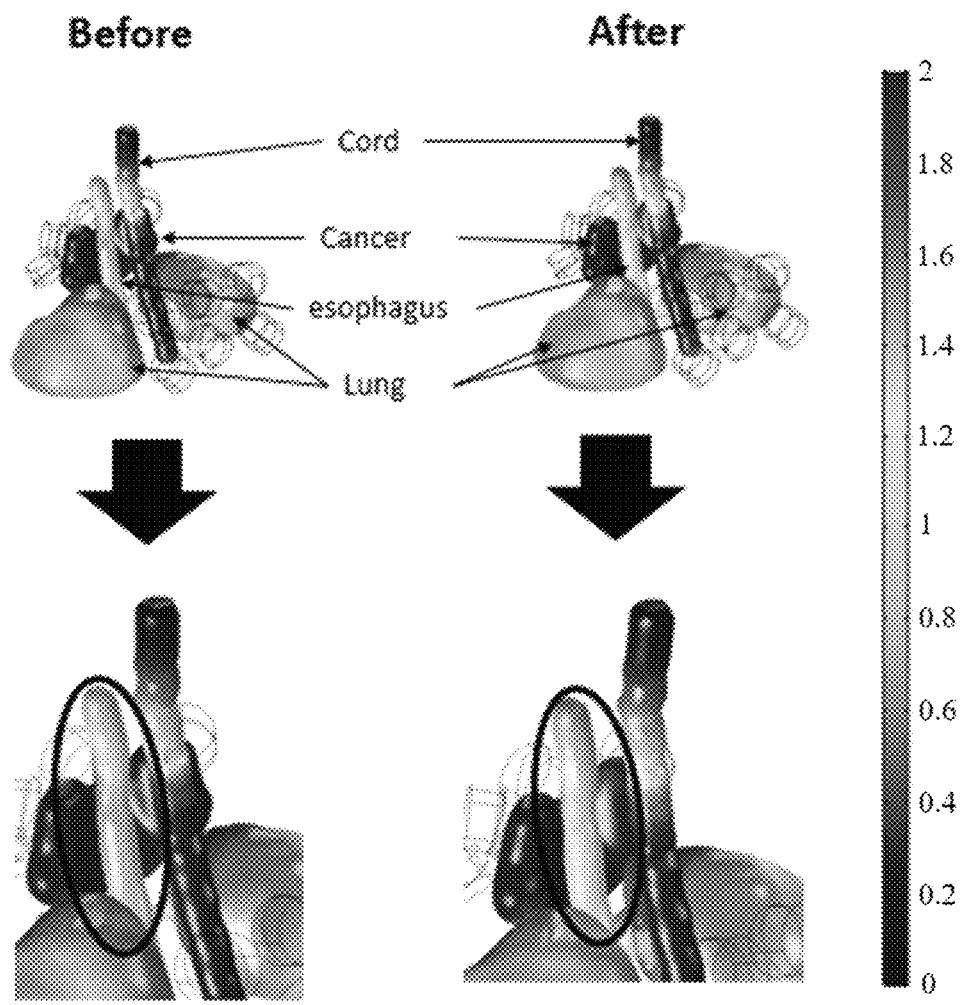
FIGS. 4 and 5 show diagrams comparing simulations by an apparatus for alternating electric fields therapy using an optimization algorithm, as embodied in the present disclosure, and the conventional method.
Figure 5:
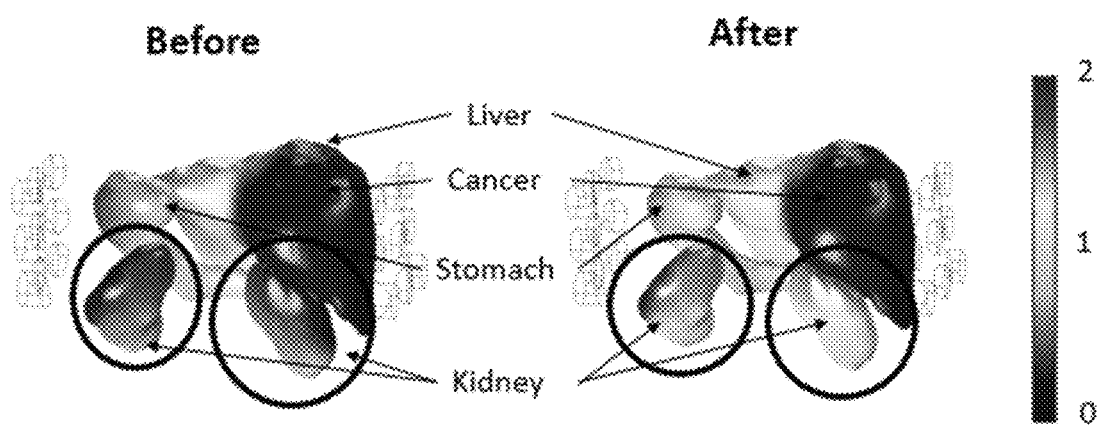

FIGS. 4 and 5 show diagrams comparing simulations by an apparatus for alternating electric fields therapy using an optimization algorithm, as embodied in the present disclosure, and the conventional method.

FIG. 4 shows the electric field distributions when the same voltage is applied to all electrodes in the conventional manner (before) and when different voltages are applied to the electrodes using the electric field optimizer (after).

Two pictures below the arrow in FIG. 4 show an enlarged simulation of the throat. The red color, indicating high electric field intensity, shows that this intensity is reduced when different magnitudes of voltages are applied using the electric field optimizer.

Table 1 lists the findings of a quantitative analysis of the results shown in FIG. 4. $V_{30}$, $V_{60}$ and $V_{90}$ denote the relative volumes to which 30% (1.5 V/cm×0.3=0.45 V/cm), 60% and 90% of the prescribed electric field intensity, respectively, are transmitted, and Eave denotes the average electric field intensity transmitted to organs. Comparisons before and after the application of the electric field optimizer show that the optimizer reduces the electric field intensity transmitted to major organs.

TABLE 1

| Thyroid | Before | After | Difference | Before | After | Difference |
|---|---|---|---|---|---|---|
| | | Cord | | | Esophagus | |
| $V_{30}$ | 82 | 80 | 2 | 100 | 100 | 0 |
| $V_{60}$ | 72 | 68 | 4 | 94 | 88 | 6 |
| $V_{90}$ | 61 | 58 | 3 | 38 | 8 | 30 |
| Eave | 1.486 | 1.380 | 0.106 | 1.301 | 1.150 | 0.151 |
| | | Right lung | | | Left lung | |
| $V_{30}$ | 100 | 100 | 0 | 100 | 100 | 0 |
| $V_{60}$ | 79 | 80 | −1 | 81 | 76 | 5 |
| $V_{90}$ | 38 | 38 | 0 | 36 | 30 | 6 |
| Eave | 1.246 | 1.258 | −0.012 | 1.220 | 1.148 | 0.072 |

FIG. 5 shows the electric field distributions when the same voltage is applied to all electrodes in the conventional manner (before) and when different voltages are applied to the electrodes using the optimization algorithm (after).

Assessments of the kidneys show that the area of red color, indicating high electric field intensity, is smaller after than before applying the optimization algorithm.

Table 2 lists the findings of a quantitative analysis of the results in FIG. 5, showing that the indicator values are all reduced after application of the electric field optimizer. That is, the electric field intensity transmitted to normal organs is greatly reduced after application of the electric field optimizer.

TABLE 2

| | Stomach | | | Right kidney | | | Left Kidney | | |
|---|---|---|---|---|---|---|---|---|---|
| Liver | Before | After | Difference | Before | After | Difference | Before | After | Difference |
| $V_{30}$ | 100 | 100 | 0 | 100 | 100 | 0 | 100 | 100 | 0 |
| $0_{60}$ | 100 | 84 | 16 | 100 | 100 | 0 | 100 | 100 | 0 |
| $V_{90}$ | 25 | 11 | 14 | 94 | 50 | 44 | 92 | 71 | 21 |
| Eave | 1.256 | 1.082 | 0.174 | 1.784 | 1.363 | 0.421 | 1.730 | 1.481 | 0.249 |

The embodiments of the present disclosure shown in the specification and drawings present a specific example to more easily describe the technical subject matter and help in understanding the present disclosure, but they are not intended to limit the scope of this disclosure. The embodiments as well as the variants based on the technical spirit of the present disclosure may be easily carried out.

The invention claimed is:

1. An apparatus for applying optimal fields using a voltage source to treat tumors in a patient by applying electric fields to the tumors and normal tissues using one or more pairs of electrode pads containing most of the electrodes, the apparatus comprising:
the voltage source,
wherein the apparatus is configured to calculate magnitudes of voltage and apply the voltage to the electrodes based on a prescribed electric field intensity for the tumors and at least one electric field intensity limit for the normal tissues,
wherein the apparatus determines an individual electric field intensity at a point in the body based on the following equation $$E_i = \sum_{i=1}^{n} w_j e_{ij}$$

and calculates an electric field object function based on the following equation $$f = \sum_{i=1}^{N} (E_i - E_0)^2$$

wherein $E_i$ is the electric field intensity value at an $i^{th}$ position, $w_j$ is a weighting of an $j^{th}$ electrode, $e_{ij}$ is an electric field intensity transmitted to the $i^{th}$ position by the $j^{th}$ electrode, f is an object function, and $E_0$ is the prescribed electric field intensity.

2. The apparatus for applying optimal fields using a voltage source of claim 1, wherein the apparatus calculates the magnitude of voltage to be applied to most of the electrodes by considering at least one of the type of the tumors to be treated, the position of the tumors and/or boundary conditions between the tumors and normal tissues.

3. The applying optimal fields using a voltage source of claim 1, wherein the apparatus calculates the magnitude of voltage of the electrodes based on an average electric field intensity of an organ.

4. The applying optimal fields using a voltage source of claim 1, wherein the electric field intensity limit is based on the organ the normal tissue comprises.

5. The applying optimal fields using a voltage source of claim 3, wherein the apparatus has an object function set using at least one of the electric field intensities transmitted to the tumors or normal organs, a weighting for each normal organ and/or the electric field intensity limit.

6. The applying optimal fields using a voltage source of claim 1, wherein the apparatus selects at least one electrode to apply voltage and selects at least one electrode to be a ground.

7. The applying optimal fields using a voltage source of claim 6, wherein the at least one electrode and the at least one ground are selected based on the prescribed electric field intensity for the tumors and the at least one electric field intensity limit for the normal tissues.

\* \* \* \* \*